(12) United States Patent
Chen (10) Patent No.: US 9,764,304 B2
(45) Date of Patent: Sep. 19, 2017

(54) ACOUSTICALLY DRIVEN NANOPARTICLE CONCENTRATOR

(75) Inventors: Sung-Wei Chen, Las Vegas, NV (US); Christopher J. Rothfuss, legal representative, Laramie, WY (US)

(73) Assignee: Empire Technology Development LLC, Wilmington, DE (US)

( * ) Notice: Subject to any disclaimer, the term of this patent is extended or adjusted under 35 U.S.C. 154(b) by 210 days.

(21) Appl. No.: 13/879,517

(22) PCT Filed: May 14, 2012

(86) PCT No.: PCT/US2012/037721
§ 371 (c)(1),
(2), (4) Date: Dec. 6, 2014

(87) PCT Pub. No.: WO2013/172810
PCT Pub. Date: Nov. 21, 2013

(65) Prior Publication Data
US 2016/0059206 A1    Mar. 3, 2016

(51) Int. Cl.
C02F 1/36 (2006.01)
B01J 19/10 (2006.01)
G10K 15/00 (2006.01)
G01N 1/40 (2006.01)
(Continued)

(52) U.S. Cl.
CPC ............ B01J 19/10 (2013.01); B01D 21/283 (2013.01); C02F 1/36 (2013.01); G01N 1/4077 (2013.01); G10K 15/00 (2013.01); B01J 2219/0801 (2013.01); B01J 2219/089 (2013.01); B01J 2219/0886 (2013.01); G01N 2001/4094 (2013.01); G01N 2015/142 (2013.01)

(58) Field of Classification Search
CPC .................. B01J 19/10; B01J 2219/089; B01J 2219/0886; B01J 2219/0801; B01J 2219/08; G10K 15/00; G01N 1/4077; G01N 2015/142; G01N 2001/4094; B01D 21/283; C02F 1/36
See application file for complete search history.

(56) References Cited

U.S. PATENT DOCUMENTS

| 4,475,921 A | 10/1984 | Barmatz |
| 4,759,775 A | 7/1988 | Peterson et al. |
| 5,164,094 A | 11/1992 | Stuckart |

(Continued)

FOREIGN PATENT DOCUMENTS

| CN | 1037463 A | 11/1989 |
| EP | 1158671 B1 | 7/2009 |

(Continued)

OTHER PUBLICATIONS

International Search Report and Written Opinion for PCT/US2012/037721 dated Aug. 16, 2012.
(Continued)

*Primary Examiner* — Walter D Griffin
*Assistant Examiner* — Cameron Allen
(74) *Attorney, Agent, or Firm* — Pepper Hamilton LLP (57) ABSTRACT

Methods and systems for concentrating and allowing for separation of nanoparticles from fluids use acoustically driven nanoparticle concentrators which have an aerogel as the reflecting material and include tuning capabilities to alter the location at which the particles are being concentrated.

13 Claims, 5 Drawing Sheets (51) Int. Cl.
*B01D 21/28* (2006.01)
*G01N 15/14* (2006.01)

(56) References Cited

U.S. PATENT DOCUMENTS

| | | | |
|---|---|---|---|
| 5,419,877 | A | 5/1995 | Goforth et al. |
| 5,626,767 | A | 5/1997 | Trampler et al. |
| 5,748,758 | A | 5/1998 | Menasco, Jr. et al. |
| 5,902,489 | A | 5/1999 | Yasuda et al. |
| 6,106,474 | A | 8/2000 | Koger et al. |
| 6,280,388 | B1 | 8/2001 | Koger et al. |
| 6,467,350 | B1 | 10/2002 | Kaduchak et al. |
| 6,475,151 | B2 | 11/2002 | Koger et al. |
| 6,603,241 | B1 | 8/2003 | Barber et al. |
| 6,644,118 | B2 | 11/2003 | Kaduchak et al. |
| 6,677,034 | B1 * | 1/2004 | Hooley ............... B06B 1/0603 102/303 |
| 6,821,554 | B2 | 11/2004 | Smith et al. |
| 6,969,420 | B2 | 11/2005 | Chien et al. |
| 7,837,040 | B2 | 11/2010 | Ward et al. |
| 2001/0014775 | A1 | 8/2001 | Koger et al. |
| 2002/0162393 | A1 | 11/2002 | Kaduchak et al. |
| 2003/0015035 | A1 | 1/2003 | Kaduchak et al. |
| 2008/0245745 | A1 | 10/2008 | Ward et al. |
| 2011/0024335 | A1 | 2/2011 | Ward et al. |
| 2014/0008307 | A1 * | 1/2014 | Guldiken ........ B01L 3/502761 210/748.05 |

FOREIGN PATENT DOCUMENTS

| | | |
|---|---|---|
| JP | H 06509406 A | 10/1994 |
| JP | 09122480 | 5/1997 |
| JP | H 09505512 A | 6/1997 |
| JP | 2002041052 A | 2/2002 |
| JP | 2008508520 A | 3/2008 |
| JP | 2008263588 | 10/2008 |
| WO | WO02/081048 A1 | 10/2002 |
| WO | WO2006/032048 A2 | 3/2006 |
| WO | WO2011/152796 A1 | 12/2011 |
| WO | WO 2011161463 A2 * | 12/2011 ........... B01D 21/283 |
| WO | WO 2012135663 A2 * | 10/2012 ........ B01L 3/502761 |

OTHER PUBLICATIONS

Aerogel, d.o.o., http://www.aerogel.si/english/1_kaj_so_aerogeli_en.htm (Printed from Internet Sep. 20, 2011.
Barmatz, et al., Acoustic radiation potential on a sphere in plane, cylindrical, and spherical standing wave fields, *J. Acoust. Soc. Am.* (Mar. 1985), 77(3):928-945.
Cabot Aerogel: Aerogel for Insulation, Daylighting, Additives—Cabor Corporation, http://www.cabot.corp.com/Aerogel (Printed from Internet Sep. 15, 2012).
Goddard, et al., Ultrasonic Particle-Concentration for Sheathless Focusing of Particles for Analysis in a Flow Cytometer, *Cytometry Part A.* (Feb. 2006), 69(2):66-74.
Goddard, et al., Analytical performance of an ultrasonic particle focusing flow cytometer, *Anal Chem.* (Nov. 15, 2007), 79(22):8740-8746.
Harris, et al., A dual frequency, ultrasonic, microengineered particle manipulator, *Ultrasonics* (Apr. 2004), 42(1-9):139-144.
Hill, et al., Modelling of layered resonators for ultrasonic separation, *Ultrasonics* (May 2002), 40(1-8): 385-392.
Pierre et al., Chemistry of Aerogels and Their Applications, *Chem. Rev.* (2002), 102:4243-4265.
Townsend, et al., Performance of a quarter-wavelength particle concentrator, *Ultrasonics* (Nov. 2008), 48(6-7):515-520.
International Search Report and Written Opinion, PCT/SG2010/000213, mailed on Jul. 26, 2010.
Aerogel Suppliers, accessed at https://web.archive.org/web/20120514050240/http://p25ext.lanl.gov/~hubert/aerogel/agel_suppliers.html, last updated on Nov. 2009, pp. 3.
Hunt et al., Silica AeroGels, accessed at https://web.archive.org/web/20070509011710/http://eande.lbl.gov/ECS/Aerogels/, last updated on Apr. 2004, pp. 3.
What is Airglass?, accessed at https://web.archive.org/web/20120620145250/http://www.airglass.se/, last updated on Jun. 8, 2004, pp. 2.

* cited by examiner

ACOUSTICALLY DRIVEN NANOPARTICLE CONCENTRATOR

CLAIM OF PRIORITY

This application is a U.S. national stage filing under 35 U.S.C. §371 of International Application No. PCT/US2012/037721, filed 14 May 2012 entitled "Acoustically Driven Nanoparticle Concentrator," the disclosure of which is incorporated by reference in its entirety.

BACKGROUND

Nanoparticulate matter on the order of hundreds of nanometers or less from anthropomorphic and natural origins has increased dramatically with modern manufacturing, pervasive use of consumer electronics, and in medical applications. Nanopollution is a generic name for all waste generated by nanodevices or during the nanomaterials manufacturing process. This kind of waste may be very dangerous because of its size. It may float in the air and might easily penetrate animal and plant cells causing unknown effects. Most human-made nanoparticles do not appear in nature, so living organisms may not have appropriate means to deal with nanowaste.

Particulates may typically be removed from a fluid using a physical filtering system. For example, in a heating-ventilation and air conditioning (HVAC) system, particulates may be removed using fiberglass or spun-bound filters, charged plates, or ceramic beads that are interposed in the fluid flow. In liquid fluids, various mechanical filters may be used to remove particulates from a liquid. However, a physical filtering system restricts the flow of the fluid resulting in higher energy costs for moving the fluid and frequent maintenance. Additionally, a physical filtering system may become easily clogged, requiring frequent changes.

One type of filterless cleaning system uses acoustic energy, particularly ultrasonic energy, to concentrate particles efficiently in fluids. The concept of using ultrasonic energy in fluids may be applied to flow cytometry, microfluidics, and other liquid phase applications. Ultrasonic energy may be used to separate out micron-size biological molecules, such as cells, etc., using fluid cavities on the order of millimeters. Acoustic energy systems, however, are bulky and have poor acoustic coupling between the acoustic cavity and the reflecting materials. Acoustic energy systems, are generally not usable for higher temperature processes such as combustion and gasification processes which typically produce significant amounts of nanoparticle pollution. Such systems also do not include tuning capabilities to focus the location of the concentrated particles to a collection site to account for variations in the particle size and/or variations which might occur in the system. Therefore, there remains a need for improved acoustic separation systems for nanoparticle removal.

SUMMARY

Presently disclosed are systems and methods of concentrating particulate matter in a fluid stream by using acoustic waves. Once concentrated, the particulate matter may be separated from the fluid stream if desired.

In an embodiment, systems for concentrating particulate matter to a desired location within a fluid stream include a concentrator for concentrating the particulate matter in a location within the fluid stream, a monitoring device for monitoring the location of the concentrated particulate matter in the fluid stream, and a positioning system for altering the location of the concentrated particulate matter in the fluid stream to the desired location.

In an additional embodiment, methods for separating particulate matter from a stream of fluid containing the particulate matter include flowing the stream of fluid containing the particulate matter through a particle concentrator, concentrating the particulate matter in a location within the fluid stream leaving at least a portion of the fluid in the fluid stream substantially particulate free, monitoring the location of the concentrated particulate matter in the fluid stream, adjusting the location of the concentrated particulate matter to a desired location within the fluid steam, and separating at least a substantial portion of the concentrated particulate matter and the at least a portion of the fluid stream that is substantially particulate free.

In a further embodiment, acoustic resonators include a cavity, an acoustic wave generator for generating an acoustic wave in at least a portion of the cavity, and a reflecting material for reflecting the acoustic wave within the cavity, the reflecting material comprising an aerogel.

DETAILED DESCRIPTION

Nanotechnology is a broad interdisciplinary area of research, development and industrial activity which has been growing rapidly. Engineered nanoparticles are being used in a number of industries that include: electronic, magnetic and optoelectronic, biomedical, pharmaceutical, cosmetic, energy and catalytic applications. Nanoparticles are often defined as particles in the size range of 1-100 nanometers (nm).

Many industrial processes produce particles that have dimensions in the nanometer size range. One example is the synthesis of carbon black by flame pyrolysis producing a powdered form of carbon. Other common materials produced by flame pyrolysis or similar thermal processes include fumed silica (silicon dioxide), ultrafine titanium dioxide (TiO$_2$) and ultrafine metals such as nickel. Other industrial processes, such as thermal spraying and coating, create and use nanosize particles as part of the process. Welding may generate ultrafine particles in a plume of aggregated nanosize particles, and nanoparticles are also produced in large quantities from diesel engines and from domestic activities such as gas cooking. Ultrafine particles are also found in the atmosphere where they originate from combustion sources (traffic, forest fires), volcanic activity, and from atmospheric gas to particle conversion processes such as photochemically driven nucleation.

Filtration is one manner in which nanoparticles may be removed from fluid sources. As the fluid passes though the filter, the trajectories of the particles deviate from the air streamline around the filter fibers and the particles may collide with the filter fibers and become deposited on them. The removal mechanisms include diffusion, interception, inertial impaction and gravitational settling. Electrostatic forces may also play a role in some filter types. Once the particle is collected onto a fiber, it will adhere to the filter fiber due to Van der Waals forces. Filters, therefore, need to be changed at regular intervals to minimally obstruct the flow path.

As an alternative to filters, acoustic particle concentrators do not require a filter to be placed in the main fluid flow stream. Described herein are illustrative systems, methods, computer-readable media, etc., for acoustic particle concentrator devices. Acoustic waves, for example, in a quarter wave resonant mode, may be generated by a multi-layer resonance structure, such as a fluid cavity, and may be used to concentrate nanoparticle pollutants in flow structures. The acoustic waves may be generated by an acoustic transducer attached to a fluid cavity. These acoustic waves may operate across a wide range of frequencies, but particularly within the audible range. Nanoparticles may be concentrated in stream and may then be diverted for separation from the stream, or for analysis, remediation, sequestration, or other uses. Audible and near-audible acoustic signals may be used to acoustically drive the resonance, for example, in standard gas exhaust ducts.

Figure 1:
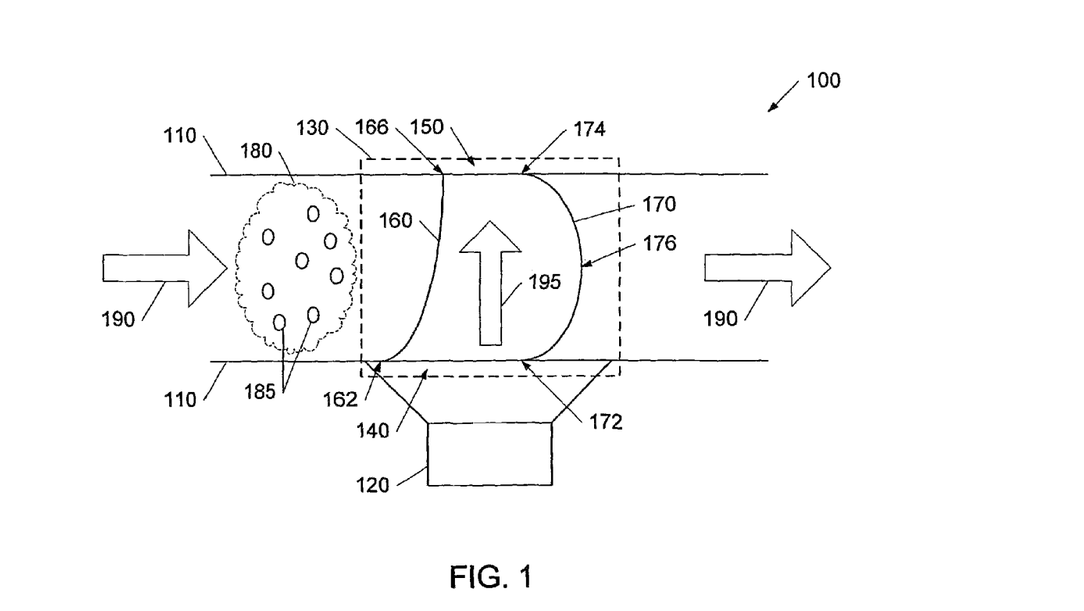
FIG. 1 is a schematic front view of an acoustic particle concentrator in accordance with an illustrative embodiment.

Referring to FIG. 1, a schematic front view of an acoustic particle concentrator 100 in accordance with an illustrative embodiment is shown. The acoustic particle concentrator 100 includes a fluid cavity 110 and an acoustic transducer 120. The fluid cavity 110 may be any enclosure or partial enclosure that may at least partially or completely contain a fluid, such as, but not limited to, a gas. A fluid is a substance that continually deforms (flows) under an applied shear stress. Fluid may be a liquid, gas, or liquid and gas together. Examples of a liquid are water, glycol, oil, etc. Examples of a gas are air, nitrogen, steam, smoke, vapor, etc. The fluid may be at any temperature, pressure, or density where it is still in a liquid or gas phase.

The fluid cavity 110 may be, for example, a duct, a pipe, a dedicated gas chamber, an enclosure, or a cyclone. For example, the fluid cavity 110 may be a HVAC duct. The fluid cavity 110 may be made of metal, plastic, or a fiber-based material. For example, the fluid cavity 110 may be made of steel, galvanized steel, stainless steel, aluminum, titanium, or any other metal. Alternatively, the fluid cavity 110 may be made of polyvinyl chloride (PVC), acrylonitrile butadiene styrene (ABS), polycarbonate, or any other plastic. The fluid cavity 110 may generally be any shape and any size. Examples of cross-section shape include square, rectangle, circle, oval, and triangle. The cross-section shape can be regular or irregular. The cross-section shape can be uniform throughout the fluid cavity 110, or can vary at different locations within the fluid cavity 110. The fluid cavity 110 in some embodiments may have a cross-section larger than several square centimeters. For example, the fluid cavity 110 may be a 7.5 cm circular duct having a cross-section of about 44 square centimeters. Alternatively, the fluid cavity 110 may be a 2 m by 2 m rectangular duct having a cross-section of about 31,416 square centimeters. Alternatively, the fluid cavity 110 may be a 1 cm circular duct having a cross-section of about 0.78 square centimeters. In an illustrative embodiment, the fluid cavity 110 may have a cross-section from about 25 square centimeters to about 900 square centimeters.

The acoustic transducer 120 may be a device that generates sound waves. For example, the acoustic transducer 120 may be a speaker, a loudspeaker, a magnetic inductive unit, a piezoelectric speaker, or any other sound generating device. The acoustic transducer 120 may be acoustically associated with at least one portion 130 of the fluid cavity 110. Acoustically associated connotes that a first object and a second object are configured so that sound waves (i.e. acoustic energy) may be transmitted from the first object to and/or through the second object with minimal attenuation (e.g. about less than 50%). The portion 130 of the fluid cavity 110 may be a section of the fluid cavity. The portion 130 of the fluid cavity 110 may include a top, a bottom, a first side, and a second side associated with a length of the fluid cavity. For example, in a duct system including several hundred meters of 25 cm×40 cm ductwork, the portion 130 of the fluid cavity 110 may be a 1 meter section of the ductwork.

In one illustrative embodiment, the acoustic transducer 120 may be directly attached to the portion 130 of the fluid cavity 110 such that sound generated by the acoustic transducer may be transmitted into the inside of the portion of the fluid cavity. In another illustrative embodiment, the portion 130 of the fluid cavity 110 may itself be part of the acoustic transducer 120. For instance, when a piezoelectric is attached to a heating duct, the material of the heating duct may act as a diaphragm of an acoustic transducer. Alternatively, an acoustic transducer 120 may be built into a fluid cavity 110.

The acoustic transducer 120 may generate a single acoustic frequency or multiple acoustic frequencies in series or simultaneously. The frequencies may be selected to affect particular particles as discussed further below. The acoustic transducer 120 may also generate music. The music may be selected to include particular frequencies at particular power levels. For example, the frequency may be in a range from 0 Hz to about 60 kHz and the power level may be in a range from 0 decibels to about 200 decibels.

One or more acoustic transducers may be located along the portion 130 of the fluid cavity 110. For example, an acoustic transducer may be located on each side of a rectangular duct. In another example, acoustic transducers may be located around the outside of a circular duct. Each acoustic transducer may be designed for a different frequency range or the same frequency range or combinations thereof. In another illustrative embodiment, the entire fluid cavity 110 may be acoustically associated with one or more acoustic transducers.

The portion 130 of the fluid cavity 110 may be configured as a resonator. In one illustrative embodiment, the portion 130 of the fluid cavity 110 may be configured as a quarter-wavelength resonator. A first side 140 of the portion 130 of the fluid cavity 110 and a second side 150 of the portion of the fluid cavity are located a quarter-wavelength ($\lambda/4$) apart from each other. The acoustic transducer 120 may be located on the first side 140. Thus, when the acoustic transducer 120 forms an acoustic wave with wavelength λ, a quarter-wavelength standing wave 160 may be formed in the portion 130 of the fluid cavity 110. The quarter-wavelength standing wave 160 includes a node 162 at the first side 140 and an antinode 166 at the second side 150. At node 162, acoustic power is at a minimum, and at antinode 166 acoustic power is at a maximum.

In another illustrative embodiment, the portion 130 of the fluid cavity 110 may be configured as a half-wavelength resonator. The first side 140 of the portion 130 of the fluid cavity 110 and the second side 150 of the portion of the fluid cavity are located a half-wavelength (λ/2) apart from each other. In the illustrated embodiment, the acoustic transducer 120 may be located on the first side 140. Thus, when the acoustic transducer 120 forms an acoustic wave with wavelength λ, a half-wavelength standing wave 170 may be formed in the portion 130 of the fluid cavity 110. The half-wavelength standing wave 170 includes nodes 172, 174 at the first side 140 and the second side 150 and an antinode 176 halfway between the first side 140 and the second side 150. At nodes 172, 174, acoustic power is at a minimum, and at antinode 176 acoustic power is at a maximum.

Alternatively, the portion 130 of the fluid cavity 110 may be configured such that other fractional standing waves may be formed. The portion 130 of the fluid cavity 110 may be designed such that various areas of the portion of the fluid cavity may generate standing waves based on different wavelengths. In addition, the portion 130 of the fluid cavity 110 may be configured to generate two-dimensional standing waves. For example, a two-dimensional standing wave may be produced using a transducer for each dimension, a transducer in one dimension and a reflector in the other, or transient acoustic excitations that are three-dimensional and that are designed so that a traveling wave sequence generates two-dimensional or three-dimensional standing waves in concert with the resonance structure. Two-dimensional and three-dimensional standing waves may be generated and controlled using a computer adapted to control the transducers.

The fluid cavity 110 may direct, confine, or contain a fluid 180. The fluid 180 may be, for example, a gas or a liquid. The fluid 180 may be for heating, cooling, or moving a material dispersed within the fluid. In one illustrative embodiment, the gas may be ambient air, heated air, air-conditioned air, humidified air, or refrigerated air. In another illustrative embodiment, the gas may be an industrial gas, medical gas, or specialty gas such as purified nitrogen, oxygen, argon, or carbon dioxide. In one illustrative embodiment, the liquid may be a cooling liquid, a heating liquid, or a liquid for moving material such as water, glycol, or ammonia.

The fluid 180 contains particulate 185. The particulate 185 may include particles of various sizes, shapes, weight, density, and material. For instance, the particulate 185 may include, but is not limited to, nanoparticles, dust, bacteria, microbes, viruses, spores, molecules, or macromolecules. The particulate 185 may generally be any size. Example sizes include about 0.01 microns to about 10 microns in diameter. The particulate 185 may also be about 10 microns to about 25 microns in diameter, or about 25 microns to about 50 microns in diameter. Example sizes include about 0.01 microns, 0.1 microns, 1 micron, 5 microns, 10 microns, 15 microns, 20 microns, 25 microns, 30 microns, 35 microns, 40 microns, 45 microns, 50 microns, and ranges between any two of these values. Examples of particulate may include dust, dirt, and fly ash. Nanoparticles may be considered any particle from about 0.1 microns to about 0.5 microns in diameter. Nanoparticles could also include any particle from about 0.5 microns to about 1 microns in diameter, or about 1 micron to about 5 microns in diameter. Examples of nanoparticles may include dust, dirt, and waste from nanotechnology fabrication processes, particles produced as waste or as product from chemical reactions, chemicals, and other airborne contaminants. In one illustrative embodiment, the fluid 180 flows along the direction of arrows 190.

When the acoustic transducer 120 is activated, an acoustic wave is generated. The acoustic transducer 120 may be activated manually by a switch, a detector, or by an automated control system. The acoustic wave may move the particulate 185 towards the second side 150. Thus, an acoustic force represented by arrow 195 is generated. The acoustic wave is selected to increase the concentration of the particulate 185 in a location in the fluid cavity 110. When the portion 130 of the fluid cavity 110 is a quarter-wavelength resonator, the location in the fluid cavity is at the antinode 166 at the second side 150. Since the quarter-wave creates a node with energy maxima near or at the top of the chamber, the acoustic wave energy drives nanoparticles differentially to the top of the flow. When the portion 130 of the fluid cavity 110 is a half-wavelength resonator, the location in the fluid cavity is at the antinode 176 in the middle of the fluid cavity. Using a resonance structure that allows half-wave resonance collects particles at the mid-point of the fluid cavity. Hence, various particle collection configurations are possible allowing for various particle collection points.

The acoustic force ($F_{ac}$) experienced by particles in the gas is proportional to the third power of the particle radius such that:

$$F_{ac} = 4\pi\varepsilon\bar{k}R^3\Phi(\beta, \rho)\sin(2ky)$$

$$\varepsilon = \frac{1}{2}\rho\left(u(x^2) + \frac{p(x)^2}{(\rho c)^2}\right)$$

$$\Phi = \frac{\rho_p + \frac{2}{3}(\rho_p - \rho_f)}{2\rho_p + \rho_f} - \frac{c_f^2\rho_f}{3c_p^2\rho_p}$$

where R is the particle radius, ρp is the particle density, Φ is the acoustic contrast, k is the wave number, ε is the time averaged energy density of the acoustic wave, u(x) is the acoustic velocity field, p(x) is the pressure field, cp is the sonic velocity of the particle, cf is the sonic velocity of the fluid, and ρf is the density of the fluid.

In one illustrative embodiment, the radius of a nanoparticle (e.g., about a 10 nm radius) differs from the radius of a gas molecule (e.g., about 100 Angstroms) by about two orders of magnitude. Since the force experienced by particles in the flow varies proportionally to the third power of their radii, this implies that, relative to a gas molecule, a nanoparticle experiences a force differential of over $10^6$. Thus the relatively large nanoparticles may be efficiently separated from the gas. The acoustic particle concentrator may operate on almost any carrier gas including, but not limited to, ambient air, heated air, air-conditioned air, humidified air, refrigerated air, industrial gas, medical gas, or specialty gas such as purified nitrogen, oxygen, argon, or carbon dioxide. Gas and nanoparticle radii usually differ by at least an order of magnitude, ensuring a sufficient force differential. The acoustic power of the acoustic wave may be selected manually. In practice, the optimal acoustic power may depend on the efficiency of the resonance of the portion of the fluid cavity, particle concentration, etc. The acoustic power of the acoustic wave may be, for example, in a range from 0 dB (1 mW) to 160 dB (10,000 W).

Advantageously, the particulate may be easily removed or re-directed thereby purifying the main fluid flow. For example, the particulate may be diverted to a collection point corresponding to a node or antinode as described above. At the collection point, the particulate may be diverted to another duct or filtered. Advantageously, the acoustic particle concentrator is unobtrusive to the main fluid flow.

Figure 2:
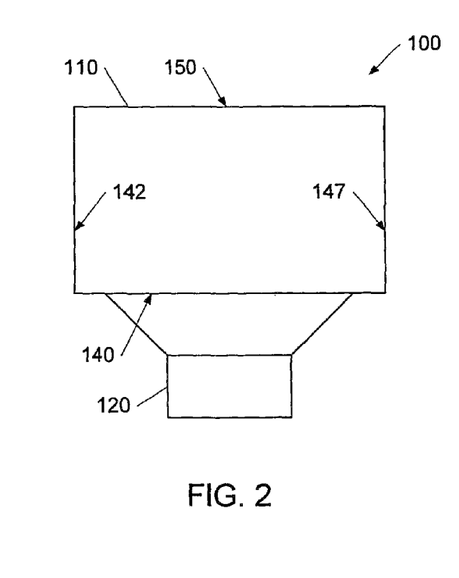
FIG. 2 is a schematic side view of the acoustic particle concentrator of FIG. 1 in accordance with an illustrative embodiment.

Referring to FIG. 2, a schematic side view of the acoustic particle concentrator 100 of FIG. 1 in accordance with an illustrative embodiment is shown. The acoustic particle concentrator 100 includes the fluid cavity 110 and the acoustic transducer 120 as described above. The cross-section of the fluid cavity 110 may be a rectangular shape, however, any other regular or irregular shape may be used. The fluid cavity 110 may be defined by the first side 140, the second side 150, a third side 142, and a fourth side 147, and the first side may be opposite of the second side.

Figure 3:
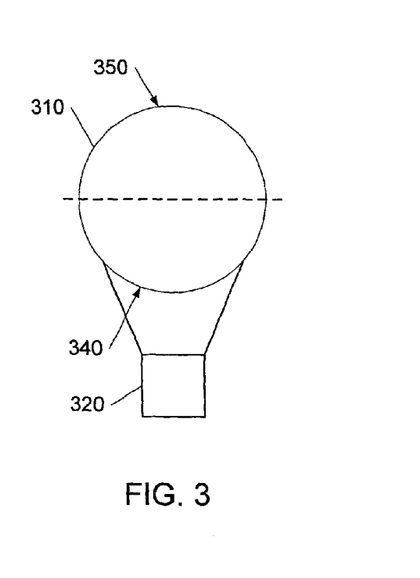
FIG. 3 is a schematic side view of an acoustic particle concentrator with a circular cross-section in accordance with an illustrative embodiment.

Referring to FIG. 3, a schematic side view of an acoustic particle concentrator with a circular cross-section in accordance with another illustrative embodiment is shown. The acoustic particle concentrator with a circular cross-section includes a fluid cavity 310 and an acoustic transducer 320 as described above. The cross-section of the fluid cavity 310 may be a circular shape, however, any other shape may be used. The fluid cavity 310 may be defined by a first side 340 and a second side 350.

Figure 4:
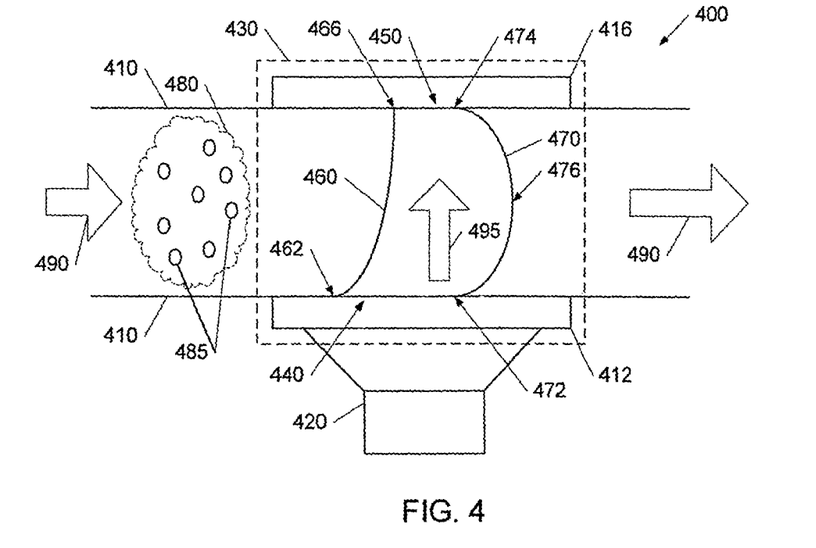
FIG. 4 is a schematic front view of an acoustic particle concentrator including impedance materials in accordance with an illustrative embodiment.
Figure 5:
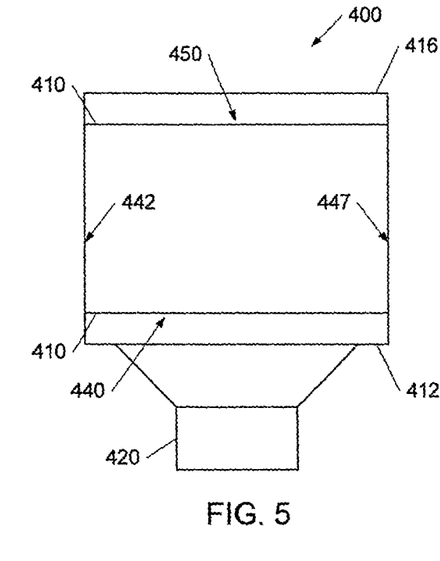
FIG. 5 is a schematic side view of the acoustic particle concentrator including impedance materials of FIG. 4 in accordance with an illustrative embodiment.
Figure 6:
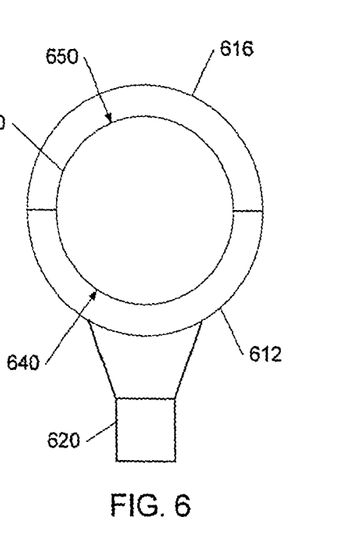
FIG. 6 is a schematic side view of an acoustic particle concentrator including impedance materials with a circular cross-section in accordance with an illustrative embodiment.

Referring to FIG. 4, a schematic front view of an acoustic particle concentrator including impedance materials 400 in accordance with still another illustrative embodiment is shown. The acoustic particle concentrator including impedance materials 400 includes a fluid cavity 410 and an acoustic transducer 420. The fluid cavity 410 may be a duct, a pipe, an enclosure, or a cyclone, as described above.

The acoustic transducer 420 may be a speaker, a loudspeaker, a magnetic inductive unit, a piezoelectric speaker, or any other sound generating device. The acoustic transducer 420 may be acoustically associated with a portion 430 of the fluid cavity 410. In one illustrative embodiment, the acoustic transducer 420 may be directly attached to the fluid cavity 410 such that sound generated by the acoustic transducer may be transmitted into the inside of the portion 430 of the fluid cavity. The acoustic transducer 420 may be attached to the portion 430 of the fluid cavity 410 using screws, rivets, straps, adhesive, or any other kind of fastener. In another illustrative embodiment, the portion 430 of the fluid cavity 410 may itself be part of the acoustic transducer 420. For instance, when a piezoelectric element is attached to a heating duct, the material of the heating duct may act as a diaphragm of an acoustic transducer. Alternatively, an acoustic transducer 420 may be built into a fluid cavity 410.

The acoustic transducer 420 may generate a single acoustic frequency or multiple acoustic frequencies in series or simultaneously. The acoustic transducer 420 may also generate music. The music may be selected to include particular frequencies at particular power levels, as described further below.

One or more acoustic transducers may be located along the at least a portion 430 of the fluid cavity 410. For example, an acoustic transducer may be located on each side of a rectangular duct. In another example, acoustic transducers may be located around the outside of a circular duct. Each acoustic transducer may be designed for a different frequency range. In another illustrative embodiment, the entire fluid cavity 410 may be acoustically associated with an acoustic transducer.

The portion 430 of the fluid cavity 410 may be configured as a resonator. In one illustrative embodiment, the portion 430 of the fluid cavity 410 may be configured to be a quarter-wavelength resonator. A first side 440 of the portion 430 of the fluid cavity 410 and a second side 450 of the portion of the fluid cavity are located a quarter-wavelength ($\lambda/4$) apart from each other. The acoustic transducer 420 may be located on the first side 440. Thus, when the acoustic transducer 420 forms an acoustic wave with wavelength ($\lambda$) a quarter-wavelength standing wave 460 is formed in the portion 430 of the fluid cavity 410. The quarter-wavelength standing wave 460 includes a node 462 at the first side 440 and an antinode 466 at the second side 450. At node 462, acoustic power is at a minimum and at antinode 466, acoustic power is at a maximum.

In another illustrative embodiment, the portion 430 of the fluid cavity 410 may be configured to be a half-wavelength resonator. The first side 440 of the portion 430 of the fluid cavity 410 and the second side 450 of the portion of the fluid cavity are located a half-wavelength ($\lambda/2$) apart from each other. The acoustic transducer 420 may be located on the first side 440. Thus, when the acoustic transducer 420 forms an acoustic wave with wavelength ($\lambda$) a half-wavelength standing wave 470 is formed in the portion 430 of the fluid cavity 410. The half-wavelength standing wave 470 includes nodes 472, 474 at the first side 440 and the second side 450 and an antinode 476 halfway between the first side and the second side. At nodes 472, 474, acoustic power is at a minimum and at antinode 476, acoustic power is at a maximum.

Alternatively, the portion 430 of the fluid cavity 410 may be configured such that other fractional standing waves may be formed. The portion 430 of the fluid cavity 410 may be designed such that various areas of the portion of the fluid cavity may form standing waves based on different wavelengths. In addition, the portion 430 of the fluid cavity 410 may be configured to form two-dimensional standing waves.

In addition, the portion 430 of the fluid cavity 410 may include acoustic impedance materials selected to enhance the production and effectiveness of acoustic waves generated by the acoustic transducer 420. The acoustic impedance of a material is determined by both the speed at which sound travels through the material and the amount of acoustic energy absorbed by the material. For example, foam has a high acoustic impedance since sound does not travel well through foam and foam absorbs acoustic energy. Conversely, metal has a low acoustic impedance since sound travels well through it and metal tends to transfer acoustic energy well.

The first side 440 may include an impedance matching material 412. The impedance matching material 412 allows acoustic waves generated by the acoustic transducer 420 to pass to the portion 430 of the fluid cavity 410 with minimal attenuation. The impedance matching material 412 may be a metal or any other material that transmits the acoustic wave with minimal attenuation, such as galvanized sheet metal. In one illustrative embodiment, the fluid cavity 410, itself, may be made of impedance matching material. In another illustrative embodiment, the impedance matching material may have a high speed of sound, i.e. greater than 343 meters per second (the speed of sound in air).

The second side 450 may include a reflectance material 416. The reflectance material 416 allows acoustic waves generated by the acoustic transducer 420 to reflect off of the second side 450 and back into the fluid cavity 410 thereby promoting a standing wave. The reflectance material 416 may be any material that results in a manageable thickness, as described below. The reflectance material 416 may have a low speed of sound, i.e. less than 343 meters per second. The thickness of the reflectance material 416 relative to the second side 450 may be selected based on the wavelength of the selected acoustic wave as described further below. The reflectance material 416 may be located on the exterior of the fluid cavity 410 as shown in FIG. 4, or may be located within the cavity as shown schematically in FIG. 7.

Some examples of materials which may be used as the reflectance material are cork, synthetic rubber, buna rubber, or an aerogel, such as a silica aerogel. Aerogels are low-density solid state materials derived from gel in which the liquid component is replaced with gas (which may be 90% of the structure). Aerogels exhibit relatively low thermal conductivities for a solid, are exceptional reflectors of sound, and have very low sound velocity through their structure (about 100 m/s). Silica aerogels have high temperature stability, with degradation temperatures greater than about 750° C., enabling silica aerogels to be used as the reflecting material in nanoparticle concentrators in high temperature combustion or gasification processes. Such a high-temperature concentrator may also be coupled with a native process, for example, scrubbing a waste stream of a native process with a high temperature treatment, which may be followed by cleaning with a nanoparticle concentrator. The speed of sound in silica aerogels is about 70 m/s, thus allowing for a significantly thinner layer of reflecting material to be used as described further below.

When the acoustic transducer 420 forms an acoustic wave, the acoustic wave travels through the impedance matching material 412 at the first side 440 and into the fluid cavity 410. The acoustic wave travels through the portion 430 of the fluid cavity 410. When the acoustic wave reaches the second side 450, the reflectance material 416 reflects the acoustic wave back towards the first side 440 thereby creating a standing wave in the portion 430 of the fluid cavity 410.

The fluid cavity 410 may direct, confine, or contain a fluid 480. The fluid 480 may be, for example, a gas or a liquid. In one illustrative embodiment, the gas may be ambient air. The fluid 480 contains particulate 485, which may include particles of various sizes, shapes, weight, density, or material. For instance, the particulate 485 may include nanoparticles, dust, bacteria, microbes, viruses, spores, molecules, or macromolecules. The particulate 485 may be any size as previously described but may typically be about 10 nm to about 10 microns in diameter. In one illustrative embodiment, the fluid 480 flows along the direction of arrows 490.

When the acoustic transducer 420 is activated, an acoustic wave is generated. The acoustic transducer 420 may be activated manually by a switch, a detector, or by an automated control system. The acoustic wave may move the particulate 485 towards the second side. Thus, an acoustic force represented by arrow 495 is generated. The acoustic wave may be selected to increase the concentration of the particulate 485 in a location in the fluid cavity 410. When the portion 430 of the fluid cavity 410 is a quarter-wavelength resonator, the location in the fluid cavity is at the antinode 466 at the second side 450. Since the quarter-wave creates a node with energy maxima near or at the top of the chamber, the acoustic wave energy drives nanoparticles differentially to the top of the flow. When the portion 430 of the fluid cavity 410 is a half-wavelength resonator, the location in the fluid cavity is at the antinode 476 in the middle of the fluid cavity 410. A resonance structure that allows half-wave resonance collects particles at the mid-point of the fluid cavity.

Referring to FIG. 5, a schematic side view of the acoustic particle concentrator including impedance materials 400 of FIG. 4 in accordance with an illustrative embodiment is shown. The acoustic particle concentrator including impedance materials 400 includes the fluid cavity 410 and the acoustic transducer 420 as described above. The cross-section of the fluid cavity 410 may be a rectangular shape, however, any other shape may be used. The fluid cavity 410 may be defined by the first side 440, the second side 450, a third side 442, and a fourth side 447. The first side 440 may be opposite of the second side 450. The first side 440 includes the impedance matching material 412. The second side 450 includes the reflectance material 416.

Referring to FIG. 6, a schematic side view of an acoustic particle concentrator including impedance materials with a circular cross-section in accordance with another illustrative embodiment is shown. The acoustic particle concentrator with a circular cross-section includes a fluid cavity 610 and an acoustic transducer 620 as described above. The cross-section of the fluid cavity 610 may be a circular shape, however, any other shape may be used. The fluid cavity 610 may be defined by a first side 640 and a second side 650. The first side 640 includes the impedance matching material 612. The second side 650 includes the reflectance material 616.

The acoustic particle concentrator including impedance materials may have a fluid cavity of a quarter wavelength and a reflector material thickness of a half wavelength (scaled for the proper speed of wave propagation within the reflector material) as follows:

$$\frac{c_r}{f} = 2t_r, \frac{c_g}{f} = 4t_g$$

where $c_r$ is the velocity of sound in the reflector, $c_g$ is the velocity of sound in the gas, f is the frequency of the acoustic wave, $t_r$ is the thickness of the reflector, and $t_g$ is the distance across the fluid cavity.

Referring to FIG. 7, a schematic front view of an acoustic particle concentrator system 700 in accordance with an illustrative embodiment is shown. The acoustic particle concentrator system 700 includes a fluid cavity defined by duct walls 710 and an acoustic transducer 720. The acoustic transducer 720 may be acoustically associated with a portion of the fluid cavity 730. The fluid cavity 710 may be defined by a first side 740 and a second side 750. The first side 740 includes an impedance matching material 712. The second side 750 includes an aerogel reflectance material 716. The impedance matching material 712 and reflectance material 716 may be located along the portion of the fluid cavity 730 or the entire fluid cavity 710.

In an embodiment in which the reflectance material may be an aerogel the reflectance material 716 may be located within the ductwork 710 due to its higher thermal stability. To make the aerogel resistant to the materials passing through the system, the aerogel may be coated with a refractory material. By including such a refractory coating, the aerogel may not absorb materials which are passing over the aerogel, while at the same time remaining unobstructive to the flow of fluid. The coating may be any of the refractory metals niobium, molybdenum, tantalum, tungsten, rhenium, titanium, vanadium, chromium, zirconium, hafnium, ruthenium, osmium, iridium, rhodium, or combinations thereof.

Essentially any other refractory material which may withstand temperatures of at least about 750° C. may be usable as a coating material for the aerogel. Titanium has been found to bond well to aerogels. A 500 nm to several micron thick coating may inhibit absorption by the aerogel while allowing for good acoustic coupling to the interior walls of a particle concentrator.

Figure 7:
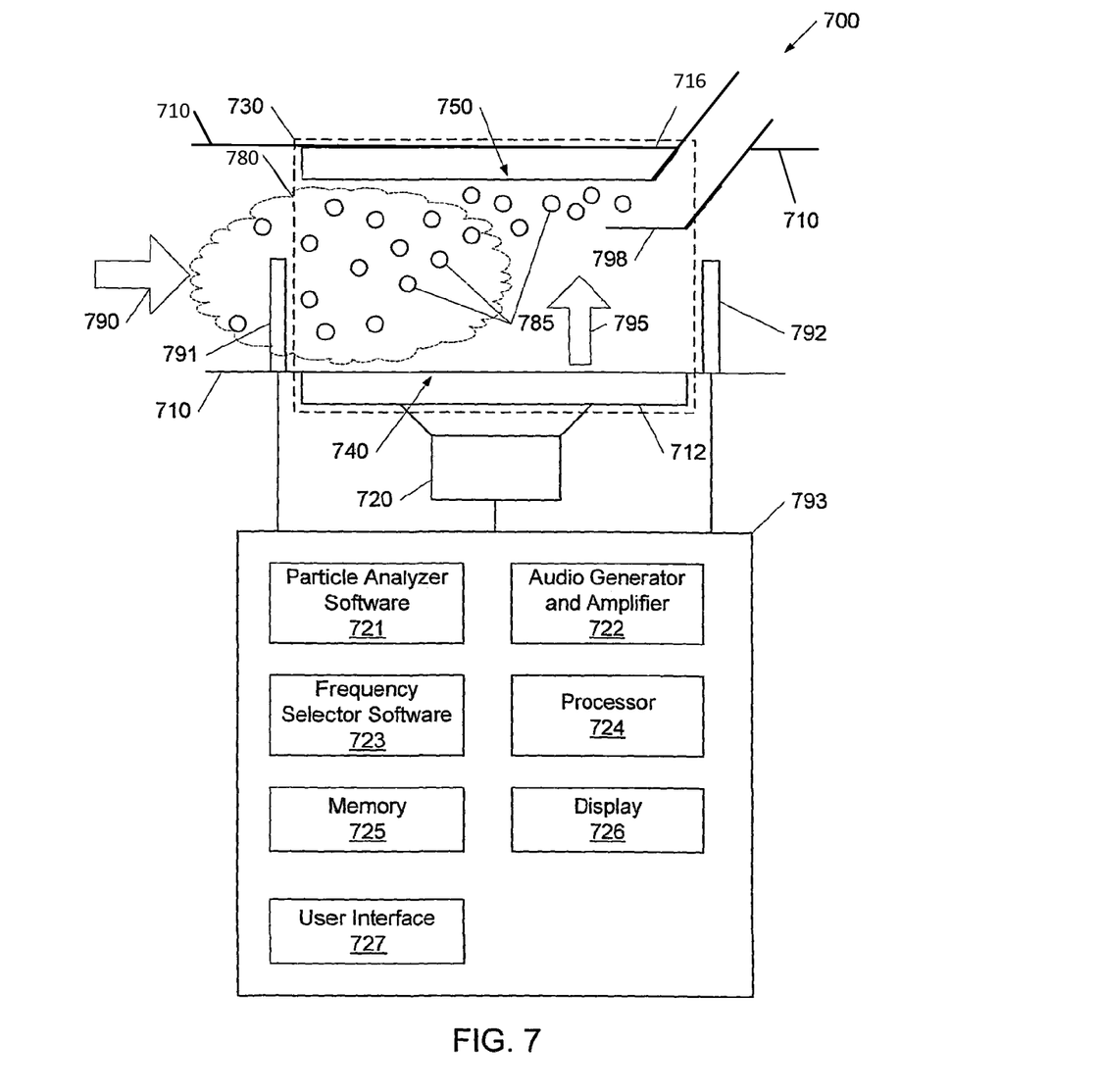
FIG. 7 is a schematic front view of an acoustic particle concentrator system in accordance with an illustrative embodiment.

The fluid cavity 710 may direct, confine, or contain a fluid 780. The fluid 780 may be, for example, a gas or a liquid. In one illustrative embodiment, the gas may be ambient air. The fluid 780 contains particulate 785 which may include particles of various sizes, shapes, weight, density, or material. For instance, the particulate 785 may include nanoparticles, dust, bacteria, microbes, viruses, spores, molecules, or macromolecules. The particulate 785 may be any size as previously described but may typically be about 10 nm to about 10 microns in diameter. In one illustrative embodiment, the fluid 780 may flow along the direction of arrow 790.

In one illustrative embodiment, the portion of the fluid cavity 730 may be configured as a quarter-wave resonator as described above. A collector 798 may be located at an antinode of the quarter-wave resonator. For example, the collector 798 may be located on the second side 750 of the portion of the fluid cavity 730. The collector 798 may trap, filter, concentrate, reposition, divert and/or remove the particulate 785. For example, collector 798 may be a second fluid cavity or duct that diverts the particulate 785 by removing a portion of the fluid flow. The collector 798 may be positioned so that the concentrated particulate 785 may be culled, i.e., the collector may be positioned in the stream of the particulate flow. In an embodiment, the collector 798 may also include a filter. In such an embodiment, the fluid diverted to the collector may optionally be recombined with the fluid 780 in the fluid cavity 710. Alternatively, the acoustic wave may direct (i.e. push) the particulate into an opening located along the side of the fluid cavity 710. Alternatively, multiple collectors may be placed in various locations or stages within the portion of the fluid cavity 730. Each collector may be configured to collect a different kind, size, and/or density of particulate.

When the acoustic transducer 720 is activated, an acoustic wave is generated. The acoustic wave may move the particulate 785 towards the second side 750 where the collector 798 may be located. Thus, an acoustic force represented by arrow 795 is generated. The acoustic wave may be selected to increase the concentration of the particulate 785 at the location of the collector 798 by moving the particulate towards the collector.

The acoustic particle concentrator system 700 may also include one or more of a first sensor 791, a second sensor 792, and a controller 793. The first sensor 791 and the second sensor 792 may measure the concentration of particulate 785 in the fluid 780. The first sensor 791 may be located at the intake to the portion of the fluid cavity 730 in order to measure the concentration of particulate 785 in the fluid 780 that is entering the portion of the fluid cavity 730. The second sensor 792 may be located at the exhaust of the portion of the fluid cavity 730 in order to measure the concentration of particulate 785 in the fluid 780 that is leaving the portion of the fluid cavity 730 so that particle separation effectiveness may be determined. The first sensor 791 and the second sensor 792 may be, for example, thermophoretic-type sensors; however, any particle concentration sensor may be employed. In addition, other sensors may be used to determine the temperature, velocity, and type of particulate 785 and fluid 780. Examples of other sensors include, but are not limited to, pitot tubes, thermometers, and spectrometers, reflectance detectors, scattering detectors, chemical detectors, electrical detectors, magnetic detectors, and/or nuclear sensors. Detection may be determined through electrochemical reactions, impedance methods, nuclear magnetic resonance (NMR), scintillation detections, etc.

The first sensor 791 and the second sensor 792 may be communicatively coupled with the controller 793. The controller 793 controls the operation of the acoustic particle concentrator system 700. In particular, the controller 793 drives the acoustic transducer 720. The controller 793 may be a circuit, a programmable logic computer, a desktop computer, a laptop computer, or other type of computing device. The controller 793 includes one or more of particle analyzer software 721, an audio generator and amplifier 722, frequency selector software 723, a processor 724, a memory 725, a display 726, and a user interface 727. In alternative embodiments, controller 793 may include fewer, additional, and/or different components. Memory 725, which may be any type of permanent or removable computer memory, may be a computer-readable storage medium. Memory 725 may be configured to store particle analyzer software 721, frequency selector software 723, an application configured to run particle analyzer software 721, an application configured to run frequency selector software 723, captured data from the first sensor 791 and the second sensor 792, and/or other information and applications. The controller 793 may also include a communication module to receive instructions, to control auxiliary devices, and to report data. Alternatively, the operation of the acoustic particle concentrator system 700 may be controlled via a cloud computing network.

Particle analyzer software 721 may be configured to analyze data from the first sensor 791 and the second sensor 792. Particle analyzer software 721, which may be implemented as computer-readable instructions configured to be stored on memory 725, may analyze the data from the first sensor 791 to determine the components of the fluid 780. Processor 724, which may be in electrical communication with each of the components of controller 793, may be used to run the application and to execute the instructions of particle analyzer software 721. Any type of computer processor(s) may be used. For example, the particle analyzer software 721 may determine the concentration of particulate 785 in the fluid 780 as well as the kinds of particulate in the fluid. For example, the particle analyzer software 721 may determine the kind, density, weight, and kinetic energy of the constituents of particulate 785. In addition, the particle analyzer software 721 may determine what kind of gas is in the fluid cavity 730. The particle analyzer software 721 may also use data from the second sensor 792 to determine the effectiveness of the particle separation. In an embodiment, the effectiveness of the particle separation may be used as feedback to control the frequency or frequencies of the acoustic wave. In an embodiment, the detection of the presence of one or more particulates, or certain kinds of particulates, may be used as feedback to control the frequency or frequencies of the acoustic wave. In some embodiments, the feedback may indicate to turn on or off the acoustic wave.

Frequency selector software 723 may be configured to select one or more frequencies to drive the acoustic transducer 720. Frequency selector software 723, which may be implemented as computer-readable instructions configured to be stored on memory 725, may determine the one or more frequencies based on the properties of the portion of the fluid cavity 730 such as the height of the portion of the fluid cavity, the composition of the fluid 780, and the impedance matching material 712, and the reflectance material 716 as discussed above. Processor 724, which may be in electrical communication with each of the components of controller 793, may be used to run the application and to execute the instructions of frequency selector software 723. Any type of computer processor(s) may be used.

In some embodiments, the frequency selector software 723 may select frequencies that target specific materials in the particulate 785. For example, the particulate 785 may include a first particulate and a second particulate where a first density of the first particulate is greater than a second density of the second particulate. The frequency selector software 723 may select a first frequency to increase the concentration of the first particulate in a first location in the fluid cavity, and a second frequency to increase the concentration of the second particulate in a second location in the fluid cavity based on the equation:

$$F_{ac}=4\pi\epsilon kR^3\Phi(\beta,\rho)\sin(2ky)$$

which is discussed above in detail. Thus, the first particulate and the second particulate may be directed to collectors in different parts of the portion of the fluid cavity 730. However, some selected frequencies may not fully resonate given the particular dimensions and materials of a particular fluid cavity. The frequency may be in a range of about 1 Hz to about 5000 Hz; however, any frequency may be employed. The frequency selector software 723 may also select the acoustic power at which the frequency should be generated.

Alternatively, the frequency selector software 723 may select a frequency to target a specific kind of particulate. The frequency may be used to calculate the ideal dimensions of a resonant structure as discussed above. The controller 793 may direct the portion of the fluid cavity 730 to change shape. For instance, the second side 750 may be moved closer to or farther from the first side 740 thereby changing the resonant frequency of the portion of the fluid cavity 730.

The audio generator and amplifier 722 use the one or more frequencies selected by the frequency selector software 723 to drive the acoustic transducer 720. The audio generator and amplifier 722 create the selected frequency, amplify the selected frequency, and drive the acoustic transducer 720. Alternatively, the audio generator and amplifier 722 may select a song that includes the one or more frequencies selected by the frequency selector software 723. For example, when the selected frequency is 858 Hz (as indicated by Example 1 below), the selected frequency of the acoustic wave is very close to an A flat/G sharp note. Thus, music with A flat/G sharp notes may be used to drive the acoustic transducer. For example, given the abnormal predominance of A flat/G sharp notes in "Dogs of War," the third song from the 1987 album, A Momentary Lapse of Reason by Pink Floyd, the song "Dogs of War" could drive resonance in the portion of the fluid cavity. Likewise, other songs may be used. Consequently, the acoustic particle concentrator may be used as part of a music system for a building, where the music is distributed via the building ductwork.

When particle analyzer software 721 determines that the concentration of particulate 785 in the fluid 780 has surpassed a threshold, the particle analyzer software 721 may instruct the controller 793 to activate the audio generator and amplifier 722. Alternatively, the controller 793 may drive the acoustic transducer 720 continuously, intermittently, or on a timer. The acoustic transducer 720 may also be activated manually.

Display 726 may be used to display parameters of the acoustic particle concentrator system 700 such as the properties of the portion of the fluid cavity 730 including the height of the portion of the fluid cavity, the composition of the fluid 780, and the impedance matching material 712, and the reflectance material 716 as discussed above. Display 726 may be a liquid crystal display, a cathode ray tube display, or other type of.

User interface 727 allows a user to interact with controller 793 and to enter information into a user interface window. User interface 727 may include a mouse, a keyboard, a touch screen, a touch pad, etc. The user may use user interface 727 to enter or control the parameters of the acoustic particle concentrator system 700, such as the properties of the portion of the fluid cavity 730 including the height of the portion of the fluid cavity, the composition of the fluid 780, the impedance matching material 712, and the reflectance material 716 as discussed above.

Figure 8:
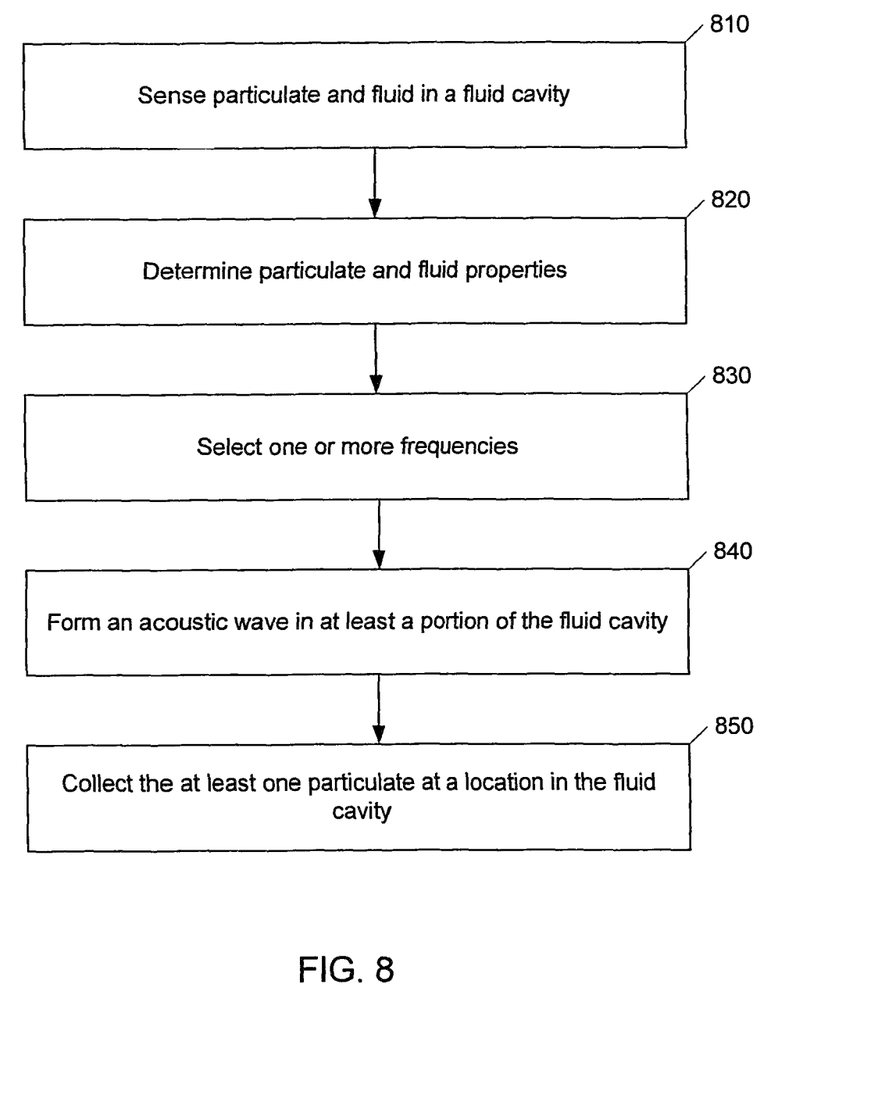
FIG. 8 is a flow diagram illustrating operations performed to concentrate particles acoustically in accordance with an embodiment.

Referring to FIG. 8, a flow diagram illustrating operations performed to concentrate particles acoustically in accordance with an illustrative embodiment is shown. In alternative embodiments, fewer, additional, and/or different operations may be performed. As shown in FIG. 8, particulate and fluid in a fluid cavity (e.g., 710) may be sensed 810, for example, by a sensor (e.g., 791 or 792). The sensor may measure 810 the concentration and other properties of particulate in a fluid in the fluid cavity. The sensor may also measure properties of the fluid.

Properties of the particulate and the fluid may also be determined 820. For example, a particle analyzer (e.g., 721) may determine 820 the concentration of particulate as well as the kinds of particulate in the fluid in the fluid cavity. The particle analyzer may determine 820 the kind, density, weight, and temperature of the constituents of particulate based on measurements from the sensor.

One or more frequencies may be selected 830. In embodiments, the frequency may be in a range of about 1 Hz to about 5000 Hz, may be any audible frequency or may be any frequency. For example, a frequency selector (e.g., 723) may select 830 one or more frequencies to drive an acoustic transducer (e.g., 720). The one or more frequencies may be selected 830 based on the properties of a portion of the fluid cavity such as the height of the portion of the fluid cavity, the composition of the fluid, an impedance matching material of the portion of the fluid cavity, and a reflectance material of the portion of the fluid cavity as discussed above. In one illustrative embodiment, the one or more frequencies may be selected 830, in part, to resonate in the fluid cavity. Alternatively, the one or more frequencies may be selected 830 to target specific kinds of particulate.

An acoustic wave may be formed 840 in the portion of the fluid cavity. Alternatively, the acoustic wave may be formed 840 in the entirety of the fluid cavity. The acoustic wave may be formed 840 based on the selected one or more frequencies. The fluid cavity may be configured as a resonator, and the acoustic wave may, therefore, resonate in the fluid cavity. The acoustic wave may concentrate particulate in the fluid cavity at a location in the fluid cavity. In one illustrative embodiment, the fluid cavity is a quarter-wave resonator. In another illustrative embodiment, the fluid cavity is a half-wave resonator. The location in the fluid cavity may be an antinode of a standing wave of the fluid cavity resonator. In another illustrative embodiment, a first particulate and a second particulate are concentrated in different locations of the fluid cavity by an acoustic wave including a first frequency and a second frequency.

The particulate may be collected 850 at the location in the fluid cavity. For example, a collector (e.g., 798) may be located at an antinode of a standing wave created by the acoustic wave in the fluid cavity resonator. The collector may trap, filter, divert and/or remove the particulate. Alternatively, multiple collectors may be placed in various locations or stages within the portion of the fluid cavity. Each collector may be configured to collect 850 a different kind, size, and/or density of particulate.

Figure 9A:
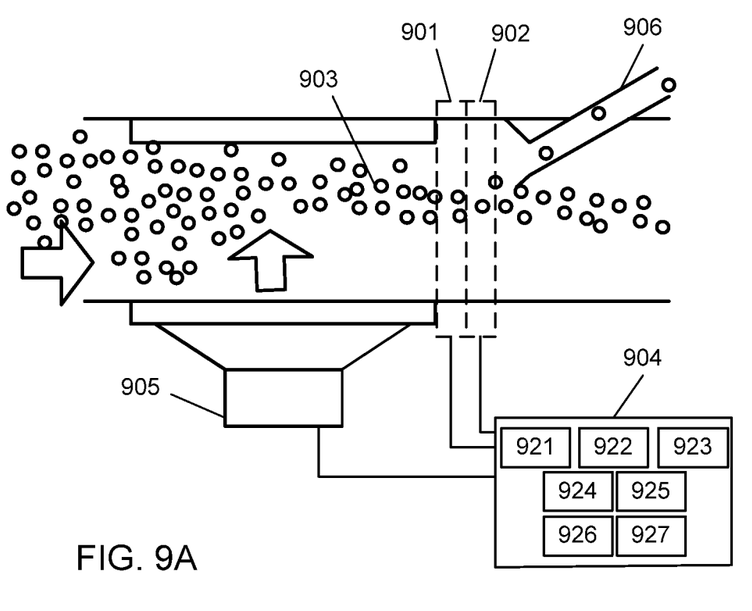
FIGS. 9A and 9B show schematic views of an acoustic particle concentrator with a position monitoring system in accordance with an embodiment.
Figure 9B:
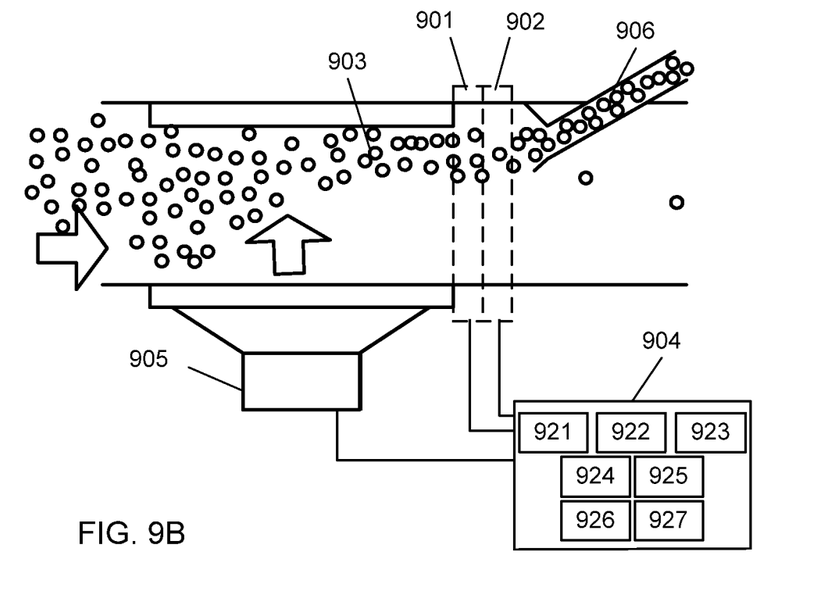

In an embodiment as represented by FIGS. 9A and 9B, the particle concentrator may also include a control system 904 which monitors the location at which the particles are being concentrated, as well as a cross-sectional area of the concentrated particle stream. There are several factors which may cause the position of the concentrated particle stream or the spread of the particle stream to change. Some of these factors include variations in the reflecting material resulting from production of the reflecting material, electrical fluctuations which may alter the power output, structural changes due to expansion and/or contraction over time, etc. As an example, the speed of sound in an aerogel reflector may be different from its nominal value of about 70 m/s. As a result, at the calculated operating frequency, the particle stream may be more or less focused than desired, or may be closer to or further from the acoustic source (depending on the node location) as shown in FIG. 9A. In either situation, an excessive amount, or possibly all of the particles 903 may not be entering the collector 906.

The location and/or spread of the stream may be monitored and altered by the control system 904. The control system may include some type of excitation source 901 that produces an excitation beam that intersects with the particles 903 to produce a detectable signal. A detector 902 may be positioned for detecting the signal generated by interaction of the excitation beam with the particles, and the signal may be monitored by the control system 904 to alter the input to the transducer 905 to change the location of the stream of particles 903 to enter the collector 906 as shown in FIG. 9B.

The excitation source 901 may be communicatively coupled with the control system 904. The control system 904 may control the operation of the acoustic particle concentrator system. In particular, the control system 904 may drive the acoustic transducer 905. The control system 904 may be a circuit, a programmable logic computer, a desktop computer, a laptop computer, or other type of computing device. The control system 904 may include analysis software 921, an audio generator and amplifier 922, wavelength, frequency, and power selector software 923, a processor 924, a memory 925, a display 926, and a user interface 927. In alternative embodiments, the control system 904 may include fewer, additional, and/or different components. Memory 925 may be any type of permanent or removable computer memory, or may be a computer-readable storage medium. Memory 925 may be configured to store position analysis software 921, software 923, an application configured to run the position analysis software 921, an application configured to run software 923, captured data from the detector 902, and/or other information and applications. The control system 904 may also include a communication module to receive instructions, to control auxiliary devices, and to report data. Alternatively, the operation of the acoustic particle concentrator system may be controlled via a cloud computing network.

Position analysis software 921 may be configured to analyze data from the detector 902, and may be implemented as computer-readable instructions configured to be stored on memory 925. The position analysis software 921 may analyze the data from the detector 902 to determine the location at which the stream is being concentrated. Processor 924, which may be in electrical communication with each of the components of control system 904, may be used to run the application and to execute the instructions of the position analysis software 921. Any type of computer processor(s) may be used.

Software 923 may be configured to select one or more wavelengths, frequencies, or powers to drive the acoustic transducer 905. The software 923, may be implemented as computer-readable instructions configured to be stored on memory 925, and may determine the frequency, wavelength and power to be used based on the position of the concentrated particles 903, properties of the portion of the fluid cavity, such as the height, the composition of the fluid, the type of impedance matching material, and the type of reflectance material as discussed above. Processor 924 may be used to run the applications and to execute the instructions of the software 923. As an alternative, the system may be a feedback system, wherein results from changes made are immediately processed and additional changes may be made, if necessary. A display 926, such as a video display, and a user interface 927, such as a keyboard, may be provided for manually viewing the operation of the system and inputting manual controls to change the system variables.

The excitation source 901 may be one of a light beam, an electron beam, an ion beam, a laser beam, or a combination thereof, and the beam may be either pulsed or continuous, or may be switchable between pulsed and continuous depending on the use. The generated signal from the particles 903 may be reflected light, laser-induced fluorescence, absorption, inelastically backscattered light, Raman scattered light, elastically scattered light, Rayleigh scattered light, Mie scattered light, or combinations thereof.

The detector 902 may include a CCD array, an intensified CCD array, an electron multiplying CCD array, an avalanche photodiode array, a silicon photodiode array, a CMOS array, a multi-anode photomultiplier tube, a photographic imaging system, a video imaging system, or any combination thereof. The control system 904 may include a data processing system for receiving the collected data from the detector 902, determining correction factors, and outputting corrected signals to the transducer 905. The control system 904 may include controls for changing a frequency of the acoustic wave, the wavelength of the acoustic wave, a power of the acoustic wave, a phase of the acoustic wave, or any combination thereof, to thereby alter the position of a node or antinode to the desired location in the fluid stream.

The location of the stream may be altered by one or more of the following: decreasing the wavelength to move the node or antinode closer to the acoustic generator, increasing the frequency to move the node or antinode closer to the acoustic generator, increasing the wavelength to move the node or antinode away from the acoustic generator, decreasing the frequency to move the node or antinode away from the acoustic generator, or changing the power to move the node or antinode toward or away from the acoustic generator. The control system 904 may operate automatically with continuous monitoring and adjustment, may be used intermittently at pre-determined time intervals, or may be controlled by a remote operator and run only when the operator wants to check the system.

A particle concentrator system may have the control system 904 of FIG. 9A alone, or in combination with the system of sensors 791, 792 and controller 793 of FIG. 7. In addition, a single processing system may be provided to operate and control both of the systems of FIGS. 7 and 9A.

Advantageously, unlike other methods that utilize vacuum or filtration to separate nanoparticles, the acoustic particle concentrator is relatively non-invasive, easy to build and run (with no moving parts), and takes advantage of a high separation potential based on the third power of the particle radii. Advantageously, the resonating structure of the acoustic particle concentrator may be built around existing or standard size exhaust systems, making integration and installation mechanics simple. Further, by using aerogels as the reflecting material, the systems may be constructed in less space since the aerogel is thinner, and may alternatively be placed inside the cavity. Aerogels also enable acoustic concentrators to be used in higher temperature processes that other filters may not be able to withstand. In addition, incorporation of a detector and feedback control system increases the efficiency of the system and may thereby result in reduced operatic costs.

EXAMPLE 1

Use of a High-Temperature Acoustic Particle Concentrator to Treat Exhaust Stream An acoustic particle concentrator can be used for filtering nanoparticles out of the exhaust stream from carbon nanotube preparation. The production of carbon nanotubes will be performed with flame pyrolysis at temperatures of about 800° C. The exhaust from the production process will have temperatures above 500° C. and will include waste particles on the order of about 5 nm or less. With reference to the illustration in FIG. 7, a ventilation duct 710, will have a diameter of about 10 cm, and will include an acoustic particle concentrator system 700.

The resonance structure will be built up around the duct (in a manner as shown in FIG. 6) and will include a loudspeaker having a frequency range of about 20 Hz to about 3 kHz as the acoustic transducer 720. The impedance matching material 712 will be the steel wall of the duct 710. Because of the high temperature, a silica aerogel coated with a 500 nm thick layer of titanium will be used as the reflectance material 716 and will be placed in the interior of the duct opposite to the loudspeaker. The ventilation duct will provide the resonant cavity, and for a quarter-wavelength resonator, a wavelength of 40 cm (duct diameter times 4) will be indicated. With the speed of sound in air of about 343 m/s the required frequency will be:

$$f = \frac{v}{\lambda} = \frac{343 \text{ m/s}}{0.4 \text{ m}} = 858 \text{ Hz} = 0.858 \text{ kHz}$$

where f is the quarter wavelength frequency, υ is velocity of sound in the medium of the fluid cavity, and λ is the wavelength associated with the quarter wavelength.

In order to obtain a speed of sound in the silica aerogel of about 70 m/s, the thickness of the silica aerogel is about:

$$\frac{c_r}{f} = 2t_r \Rightarrow t_r = \frac{c_r}{2f} = \frac{70 \text{ m/s}}{2*858 \text{ Hz}} = 0.041 \text{ m} = 4.1 \text{ cm}.$$

For comparison, the speed of sound in corks and rubbers range from about 150 m/s to about 400 m/s. Using a cork with speed of sound at about 300 m/s speed, gives a reflector made of cork a thickness of:

$$\frac{c_r}{f} = 2t_r \Rightarrow t_r = \frac{c_r}{2f} = \frac{300 \text{ m/s}}{2*858 \text{ Hz}} = 0.175 \text{ m} = 17.5 \text{ cm}.$$

Thus, an aerogel reflecting material will be less than about one-fourth the thickness of a cork reflector. While the thickness of the cork is not unreasonable for such applications, cork would not be able to withstand the high temperature of the pyrolysis exhaust. On the other hand, while steel is able to withstand the high temperature, the thickness of the steel (with speed of sound of approximately 6,000 m/s) would be increased by a factor of about 20, making the reflector on the order of meters in thickness:

$$\frac{c_r}{f} = 2t_r \Rightarrow t_r = \frac{c_r}{2f} = \frac{6000 \text{ m/s}}{2*858 \text{ Hz}} = 3.50 \text{ m}.$$

As such, steel would likely be impractical because of the thickness needed.

By applying a frequency of 858 Hz by the loudspeaker, the nanoparticles in the exhaust will be driven by the quarter wave resonance to the top of the ventilation stream, allowing for collection or diversion from the top of the stream by collector 798. An additional filter will be provided downstream of the collector 798 and out of the main air-flow stream.

EXAMPLE 2

Adjustment of Location of Particle Concentration

As described in Example 1, an acoustic particle concentrator for an exhaust stream will have a resonant cavity of 10 cm and a 4.1 cm aerogel for the reflecting material. A quarter wavelength resonance indicates a wavelength of 40 cm, and therefore a frequency of 858 kHz for the speed of sound in air of 343 m/s is required for an ideal system. During use, and with a general reference to the representation in FIG. 9A, a concentrated stream of particles 903, wherein the stream may have an approximate 1 cm diameter, will be formed and collected adjacent the reflecting material at a position about 9-10 cm from the acoustic transducer 905.

After several extreme heating and cooling cycles, the resonant chamber may experience an expansion in depth and could expand to 11 cm causing the collector 906, which may be attached to the chamber wall, to be positioned 1 cm farther from the transducer 905 at 10-11 cm. (While the anti-node would also move somewhat, for simplification of calculations and explanation, it will be assumed the antinode remains at about 10 cm from the transducer 905.) The concentrated stream of particles 903, being concentrated at 10 cm from the transducer 905, would therefore substantially miss the collector and only minimal cleaning of particulate matter would occur.

By including a control system 904 with an excitation source 901 and a detector 902, a system adjustment could be made to move the antinode away from the transducer 905 and back into alignment with the collector 906. The detector 902 and position analysis software 921 would indicate an adjustment of 1 cm is necessary to provide re-alignment, thereby providing for a resonant chamber of 11 cm. The processor 924, in conjunction with the analysis software 921 would then recalculate the frequency to move the antinode using the same equation as presented in Example 1:

$$f = \frac{v}{\lambda} = \frac{343 \text{ m/s}}{0.44 \text{ m}} = 780 \text{ Hz} = 0.780 \text{ kHz}.$$

The processor would then provide a frequency adjustment, reducing the frequency from 858 kHz to 780 kHz to realign the concentrated stream of particles 903 with the collector 906.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, may be arranged, substituted, combined, separated, and designed in a wide variety of different configurations, all of which are explicitly contemplated herein.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The present disclosure is not to be limited in terms of the particular embodiments described in this application, which are intended as illustrations of various aspects. Many modifications and variations may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which may, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," and the like include the number recited and refer to ranges which may be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for concentrating particulate matter to a desired location within a fluid stream, the system comprising:
    an acoustic resonator configured to concentrate the particulate matter in a location within the fluid stream, wherein the acoustic resonator comprises:
        a cavity;
        an acoustic transducer configured to generate an acoustic wave in at least a portion of the cavity; and
        a reflecting material configured to reflect the acoustic wave within the cavity, the reflecting material comprising a silica aerogel, wherein the silica aerogel further comprises a metal coating;
    a monitoring device configured to monitor the location of the concentrated particulate matter in the fluid stream wherein the monitoring device comprises:
        an excitation source configured to produce an excitation beam for intersecting with the fluid stream; and
        a detector array configured to detect a signal generated by interaction of the excitation beam with the particulate matter in the fluid stream; and
    a positioning system configured to alter the location of the concentrated particulate matter in the fluid stream to the desired location.

2. The system of claim 1, wherein the reflecting material further comprises, a cork, rubber, foam or a combination thereof.

3. The system of claim 1, wherein the acoustic resonator is a quarter-wave resonator or a half-wave resonator.

4. The system of claim 1, wherein the particulate matter comprises at least a first particulate having a first mass and a first concentration within the fluid stream, and at least one additional particulate having a second mass different from the first mass and a second concentration within the fluid stream, and the system further comprises:
    at least one sensor located at an intake of the at least a portion of the cavity, an exhaust of the at least a portion of the cavity or both to measure the first concentration and the second concentration; and
    a controller to adjust at least one of a frequency of the introduced acoustic wave, a power of the introduced acoustic wave, or both as a predetermined function of the first concentration and the second concentration to concentrate one of the first particulate in the desired location within the fluid stream or the at least one additional particulate in the desired location within the fluid stream.

5. The system of claim 1, wherein the positioning system comprises a control system for changing a frequency of the acoustic wave, a wavelength of the acoustic wave, a power of the acoustic wave, a phase of the acoustic wave, or any combination thereof.

6. The system of claim 1, wherein:
    the fluid is a flowing gas and the particulate matter is nanoparticulates suspended in the gas;
    the acoustic resonator concentrates the nanoparticulates in the location within the fluid stream leaving a substantially particulate free fluid portion in the fluid stream; and
    the system further comprises a separation device configured to separate the concentrated nanoparticulates and the substantially particulate free fluid portion.

7. The system of claim 6, wherein the separation device comprises at least one of:
    a filter disposed in relation to the desired location in the fluid stream to filter the concentrated nanoparticulates from the fluid stream; and
    a fluid bypass for removing a fluid portion from the fluid stream, the fluid portion comprising one of fluid containing the concentrated nanoparticulates, and fluid substantially particulate free.

8. The system of claim 1, wherein an impedance matching material is disposed between the acoustic transducer and the cavity, wherein the impedance matching material is a metal.

9. The system of claim 1, wherein the cavity is configured for flow of the fluid therethrough, the said cavity having a first side and a second side opposite the first side.

10. The system of claim 1, wherein the acoustic transducer is disposed external to the cavity and adjacent the first side for introducing an acoustic wave into at least a portion of the cavity, the introduced acoustic wave having a wavelength.

11. The system of claim 1, wherein the reflecting material is disposed adjacent the second side for reflecting the acoustic wave within the at least a portion of the cavity, the reflecting material being configured in conjunction with the wavelength of the introduced acoustic wave to produce a standing wave within the fluid cavity, the standing wave having at least one node or at least one antinode.

12. A system for concentrating particulate matter to a desired location within a fluid stream, the system comprising:
an acoustic resonator configured to concentrate the particulate matter in a location within the fluid stream, wherein the acoustic resonator comprises:
a cavity for flow of the fluid therethrough, the cavity having a first side and a second side opposite the first side;
an acoustic transducer disposed external to the cavity and adjacent the first side for introducing an acoustic wave into at least a portion of the cavity, the introduced acoustic wave having a wavelength;
an impedance matching material disposed between the acoustic transducer and the first side; and
a reflecting material comprising silica aerogel disposed adjacent the second side for reflecting the acoustic wave within the at least a portion of the cavity, the reflecting material being configured in conjunction with the wavelength of the introduced acoustic wave to produce a standing wave within the fluid cavity, the standing wave having at least one node or at least one antinode, wherein the silica aerogel comprises a metal coating to prevent sorption of constituents of the fluid stream into the aerogel; and
the location of concentrating particulate matter is substantially at the at least one node or the at least one antinode;
a monitoring device configured to monitor the location of the concentrated particulate matter in the fluid stream; and
a positioning system configured to alter the location of the concentrated particulate matter in the fluid stream to the desired location.

13. A system for concentrating particulate matter to a desired location within a fluid stream, the system comprising:
an acoustic resonator configured to concentrate the particulate matter in a location within the fluid stream, wherein the acoustic resonator comprises:
a cavity for flow of the fluid therethrough, the cavity having a first side and a second side opposite the first side;
an acoustic transducer disposed external to the cavity and adjacent the first side for introducing an acoustic wave into at least a portion of the cavity, the introduced acoustic wave having a wavelength;
an impedance matching material disposed between the acoustic transducer and the first side; and
a reflecting material disposed adjacent the second side for reflecting the acoustic wave within the at least a portion of the cavity, the reflecting material being configured in conjunction with the wavelength of the introduced acoustic wave to produce a standing wave within the fluid cavity, the standing wave having at least one node or at least one antinode; and
the location of concentrating particulate matter is substantially at the at least one node or the at least one antinode;
a monitoring device configured to monitor the location of the concentrated particulate matter in the fluid stream, wherein the monitoring device comprises:
an excitation beam for intersecting with the fluid stream, wherein the excitation beam comprises at least one of a light beam, an electron beam, an ion beam, a laser beam and any combinations thereof, and the excitation beam is at least one of a pulsed excitation beam or continuous wave excitation beam; and
a detector array configured to detect a signal generated by interaction of the excitation beam with the particulate matter in the fluid stream, wherein the generated signal comprises reflected light, laser-induced fluorescence, absorption, inelastically backscattered light, Raman scattered light, elastically scattered light, Rayleigh scattered light, Mie scattered light or combinations thereof, and wherein the detector array comprises a CCD array, an intensified CCD array, an electron multiplying CCD array, an avalanche photodiode array, a silicon photodiode array, a CMOS array, a multi-anode photomultiplier tube, a photographic imaging system, a video imaging system, or any combinations thereof; and
a positioning system configured to alter the location of the concentrated particulate matter in the fluid stream to the desired location.

* * * * *

UNITED STATES PATENT AND TRADEMARK OFFICE
CERTIFICATE OF CORRECTION

PATENT NO. : 9,764,304 B2
APPLICATION NO. : 13/879517
DATED : September 19, 2017
INVENTOR(S) : Chen Page 1 of 1

It is certified that error appears in the above-identified patent and that said Letters Patent is hereby corrected as shown below:

On the Title Page

In Item (75), under "Inventors", in Column 1, Line 1, delete "Sung-Wei Chen, Las Vegas, NV (US);" and insert -- Sung-Wei Chen, Deceased, Las Vegas, NV (US); --, therefor.

In the Specification

In Column 1, Line 46, delete "energy systems," and insert -- energy systems --, therefor.

In the Claims

In Column 22, Line 24, in Claim 2, delete "comprises, a cork," and insert -- comprises a cork, --, therefor.

Signed and Sealed this
Eighth Day of May, 2018

Andrei Iancu
*Director of the United States Patent and Trademark Office*